(12) United States Patent
Bob et al.

(10) Patent No.: US 12,048,454 B2
(45) Date of Patent: Jul. 30, 2024

(54) KNIFE CARTRIDGE AND SEALING INSTRUMENT

(71) Applicant: Erbe Elektromedizin GmbH, Tuebingen (DE)

(72) Inventors: Felix Bob, Rottenburg (DE); Stefan Kaupp, Tuebingen (DE); Linda Bauer, Rottenburg (DE); Tobias Breuninger, Riederich (DE); Bjoern Lehmann, Moessingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 781 days.

(21) Appl. No.: 17/081,014

(22) Filed: Oct. 27, 2020

(65) Prior Publication Data
US 2021/0121193 A1    Apr. 29, 2021

(30) Foreign Application Priority Data

Oct. 28, 2019 (EP) .................................... 19205674

(51) Int. Cl.
*A61B 17/3211* (2006.01)
*A61B 17/285* (2006.01)
*A61B 17/00* (2006.01)

(52) U.S. Cl.
CPC ........ *A61B 17/3211* (2013.01); *A61B 17/285* (2013.01); *A61B 2017/00778* (2013.01)

(58) Field of Classification Search
CPC . A61B 17/28; A61B 17/2812; A61B 17/2841; A61B 17/285; A61B 17/2909; A61B 2017/0023; A61B 2017/00477; A61B 2017/00778; A61B 2017/2911; A61B 17/3211; A61B 17/3213; A61B 2017/32113; A61B 18/1442; A61B 2018/1452; A61B 2018/146
See application file for complete search history.

(56) References Cited

U.S. PATENT DOCUMENTS

| 5,611,808 A | 3/1997 | Hossain et al. |
| 5,913,874 A | 6/1999 | Berns et al. |

(Continued)

FOREIGN PATENT DOCUMENTS

| CN | 104068902 A | 10/2014 |
| DE | 19637133 A1 | 3/1997 |

(Continued)

OTHER PUBLICATIONS

Extended European Search Report dated Jun. 16, 2020, in corresponding European Application No. 19205674.5, with machine English translation (20 pages).

(Continued)

*Primary Examiner* — Todd J Scherbel
(74) *Attorney, Agent, or Firm* — Fitch, Even, Tabin & Flannery LLP (57) ABSTRACT

An instrument (10) that comprises a cartridge seat (24) for a knife cartridge (25). The knife cartridge (25) holds a knife (30), preferably in protected safe position in which the blade (32) of the knife (30) is reliably retained inside the housing (26) of the knife cartridge (25) during non-use, particularly if the knife cartridge (25) is not inserted in the sealing instrument (10). This concept leads to increased handling safety for the medical staff.

16 Claims, 7 Drawing Sheets

(56) References Cited

U.S. PATENT DOCUMENTS

| | | | |
|---|---|---|---|
| 8,685,056 | B2 | 4/2014 | Evans et al. |
| 9,717,521 | B2 | 8/2017 | Gitman |
| 2003/0220637 | A1* | 11/2003 | Truckai .............. A61B 18/1442 606/51 |
| 2010/0179545 | A1 | 7/2010 | Twomey et al. |
| 2010/0292691 | A1 | 11/2010 | Brogna |
| 2011/0004208 | A1 | 1/2011 | Truckai et al. |
| 2011/0184405 | A1 | 7/2011 | Mueller |
| 2013/0046303 | A1 | 2/2013 | Evans et al. |
| 2013/0085516 | A1 | 4/2013 | Kerr et al. |
| 2014/0257284 | A1 | 9/2014 | Artale |
| 2016/0157924 | A1 | 6/2016 | Ding et al. |
| 2016/0206366 | A1 | 7/2016 | Clauda et al. |
| 2017/0143336 | A1* | 5/2017 | Shah ................ A61B 17/07207 |
| 2017/0333037 | A1 | 11/2017 | Wellman et al. |

FOREIGN PATENT DOCUMENTS

| | | |
|---|---|---|
| DE | 10 2011 012 014 A1 | 8/2012 |
| EP | 1609430 A1 | 12/2005 |
| EP | 2086440 A1 | 8/2009 |
| EP | 2245993 A2 | 11/2010 |
| EP | 2 272 454 A1 | 1/2011 |
| EP | 2489320 A2 | 8/2012 |
| EP | 2732779 A1 | 5/2014 |
| RU | 2145818 C1 | 2/2000 |
| WO | 9424947 A1 | 11/1994 |
| WO | 2018/078646 A1 | 5/2018 |

OTHER PUBLICATIONS

Partial European Search Report dated Dec. 13, 2019, in corresponding European Application No. 19205674.5, with machine English translation (19 pages).

Russian Patent Office; Office Action and Search Report in corresponding Russian Patent Application No. 2020 134 526, dated Sep. 4, 2023 (partial English translation), 18 pages.

China National Intellectual Property Administration; Office Action and Search Report in corresponding Chinese Application No. 2020111740221, dated Jan. 19, 2024, 20 pages.

* cited by examiner

KNIFE CARTRIDGE AND SEALING INSTRUMENT

RELATED APPLICATION(S)

This application claims the benefit of European Patent Application No. 19205674.5, filed Oct. 28, 2019, the contents of which is incorporated herein by reference as if fully rewritten herein.

TECHNICAL FIELD

The invention refers to a knife cartridge and a sealing instrument, particularly for sealing and dissection of vessels.

BACKGROUND

Sealing instruments are typically used in surgery in order to seal and cut vessels, e.g. blood vessels or lymphatic vessels or other tissue. During sealing a permanent vessel closure is created, wherein the vessel is separated subsequently at the closed location.

For this a sealing instrument with two jaws is known from US 2011/004208 A1 that comprise handles at their respective proximal ends. The two jaws are supported in a hinged manner at each other and form a sealing instrument with their distal ends. At one of the jaws a knife is arranged in a manner to be shiftable in distal direction that is guided in a slot of the jaw and serves for dissecting a vessel. For sealing of the vessel tissue contact surfaces of the distal parts of the two jaws can be applied with current to fuse the vessel grasped between the closed jaws.

The instrument can be used until the knife is blunted and does not create a neat cut anymore. Subsequently at least the knife must be replaced. For this the knife is accommodated in a replacement part of plastic that supports the shiftable knife element and sealing electrodes that are connected at longitudinal sections of the replacement tool that are to be connected with the distal parts of the jaws. The two longitudinal sections are connected with each other by a spring hinge such that they can follow the movement of the jaws. The replacement tool comprises an electrical connection cable that is connected with one of the jaws of the instrument.

A sealing instrument with two jaws that support one another in a hinged manner and comprise at their distal sections respective sealing electrodes for electrical sealing of vessels is known from US 2003/220637 A1. In addition, the instrument comprises a knife that is exchangeably supported and that is connected with one of the jaws in a latched manner and is then shiftably supported in distal direction.

US 2013/046303 A1 discloses an instrument with sealing electrodes and a mechanic knife that is shiftably supported in a knife channel. Instead of the mechanically movable knife in a respective receptacle of the jaws, an electrical blade can be inserted.

Similar to US 2011/004208 A1, WO 2018/078646 A1 discloses an instrument in which a replacement tool is provided that also comprises sealing electrodes and is replaceably attached at the instrument as a whole.

A further instrument with a replaceable knife is disclosed in EP 2 732 779 A1.

U.S. Pat. No. 5,913,874 A describes a sealing instrument with reusable base body and a replaceable cartridge that contains the knife as well as the sealing electrodes.

Further prior art emerges from US 2013/085516 A1, US 2016/206366A1, EP 2 245 993 A2, EP 2 086 440 A1, US 2010/179545 A1, U.S. Pat. No. 8,685,056 B2, U.S. Pat. No. 9,717,521, EP 2 489 320 A2 and DE 196 37 133 A1.

It is an object of the invention to design a sealing instrument with a replaceable knife in which the knife replacement can be carried out in a simple and safe manner. Particularly endangerment of involved personnel shall be excluded.

SUMMARY

This object is solved with the sealing instrument as well as the knife cartridge disclosed herein:

The inventive sealing instrument can be particularly configured for sealing of vessels and thereby particularly for the open surgical use. It comprises a first jaw that comprises a handle at its proximal end or is connected with such a handle. At its distal end it comprises a first tool part of a sealing tool, e.g. in form of one or more sealing electrodes. A second jaw is provided that comprises a second tool part at its distal end, e.g. again one or more sealing electrodes, and is pivotably supported with relation to the first jaw and for this, for example, pivotably connected therewith. In the proximity of the tool a cartridge seat for receiving a knife cartridge is provided.

The knife cartridge comprises a housing that encloses an inner space in which a knife is arranged. Thereby connection means can be provided by means of which the knife cartridge can be locked at the cartridge seat. At least in an instrument that is configured in a scissors-type manner with two jaws that are connected with each other in a hinged manner and scissors handles at the respective distal ends thereof the cartridge seat can be configured at one of the jaws.

The knife comprises at least one cutting edge and can be retracted into the knife cartridge and shifted out of it. For this the knife cartridge can comprise an operating device. Alternatively a coupling device for connection of the knife to an operating device can be provided. The knife is held in the inner space of the cartridge, if the cartridge is not inserted into the sealing instrument. If the knife cartridge is attached to the cartridge seat, the knife can be moved out of the knife cartridge by means of the operating device, at least thus far as it is necessary for the execution of a cut at tissue that is grasped by the instrument.

The knife replacement is carried out in that a used knife cartridge is removed from the cartridge seat and a new knife cartridge is placed thereon and is fixed there. For this means can be provided that hold the cartridge at the cartridge seat, however, release it if the legs of the instrument are transferred in a cleaning position. The cleaning position in which the cartridge is released distinguishes from other positions, i.e. the use positions, in that the two legs provided with the handles are wider opened as necessary or usual during the use of the instrument on the patient. In doing so, it is avoided that the cartridge configured as single-use part remains at the instrument during conditioning thereof.

With the inventive concept not only the danger of injuries for the involved personnel is reduced or eliminated, but concurrently a separation between single-use material in the form of the knife cartridge and an instrument part that can be sterilized is created, which is advantageous in terms of construction and cleaning aspects. Parts that are subject to no or only minor wear are part of the instrument. This applies, apart from the jaws and the hinge, particularly to the sealing electrodes. The location of the knife in a knife cartridge does not only protect from injuries, simplifies handling and allows a quicker knife replacement (insertion and removal), but concurrently a clear, smoothly shaped and easily to clean interface in the form of the cartridge seat is created. In addition, compared with a whole single-use instrument, the technical efforts for provision of instruments can be lowered and resources can be saved.

In a preferred embodiment the knife cartridge comprises a locking mechanism for locking the knife in a first position in which the blade of the knife is inside the inner space of the housing of the cartridge. Such a knife cartridge can be handled safely and stab or cut injuries of personnel handling it are excluded.

The locking mechanism comprises, at least in one possible embodiment, a blocking element movably supported at the housing of the knife cartridge to which a blocking structure is assigned that is configured at the knife. The blocking element can be a shiftable blocking element or a pivotably supported blocking element configured individually or as part of the cartridge, wherein the blocking element comprises at least one section cooperating with the blocking structure of the knife. The blocking structure of the knife can be a recess, a projection or similar. For example, the blocking element can be a blocking pin or blocking bolt that extends in or through a recess of the knife in order to block the movement of the knife. The blocking pin or blocking bolt can be movably supported in order to be brought into and out of engagement with a blocking structure of the knife. For example, for this the blocking pin can be movably supported transverse to the movement direction of the knife and comprise a recess through which the knife can be moved. If the recess is aligned with the knife, the longitudinal shifting movement of the knife is released. Is the blocking pin, however, shifted out of this release position, it extends through a blocking structure, e.g. an indentation of the knife, and thus blocks its longitudinal movement. The blocking element can, however, also be configured as integral part of the cartridge, e.g. as resilient latch or the like.

The blocking element can also be pivotably supported in order to be brought into and out of engagement with a blocking structure of the knife.

Preferably also a locking device for locking of the knife cartridge at the cartridge seat is provided. The locking device can be configured as part of the locking mechanism for locking the knife in the knife cartridge. For this the blocking element can be configured cooperating with the respective counter surface of the cartridge seat in order to unlock the knife during insertion of the knife cartridge in the cartridge seat and to lock the knife during removal of the knife cartridge from the instrument in its safe position.

The locking mechanism can particularly comprise a reciprocal interlocking that retains the knife with its blade in the knife cartridge in a first position and locks the knife cartridge at the cartridge seat in a second position in which the knife is released. Such a reciprocal interlocking can be formed, for example, by a shiftably or pivotably supported blocking element that engages in the blocking structure of the knife or in a blocking structure configured at the cartridge seat. The back and forth movement of the blocking element can be controlled by placement of the knife cartridge at the cartridge seat and by removal of the knife cartridge from the cartridge seat. Releasing of the knife cartridge locked in the instrument by the reciprocal interlocking can be effected by a movement of the two legs of the instrument, e.g. in an extended opened position that is not taken during normal use on the patient.

If the blocking structure of the knife is a recess in which the blocking element engages by a movement transverse to movement direction of the knife, the blocking element can be transferred in its knife-blocking position only if the knife is in a safe position, i.e. the blocking structure is aligned with the blocking element. In this position the blade of the knife is in a safe position within the inner space of the knife cartridge. Because the blocking element can only engage in the blocking structure of the knife in this position, it can also release the knife cartridge for removal thereof from the cartridge seat in this position.

Thus, safety for the handling personnel is obtained during insertion of the knife cartridge in the instrument, as well as during removal of the knife cartridge from the instrument.

The knife cartridge preferably comprises a knife channel that guides the knife in the cartridge in a longitudinally movable manner. This knife channel is preferably aligned with a knife channel provided at the jaw, if the cartridge is attached to the cartridge seat. The proximal part of the knife channel usually forms the part of the knife channel in an instrument that is most difficult to clean. The part of the knife channel in which the knife is in rest position is particularly difficult to access during sterilization. The knife, however, conveys dirt to this position during use. This part of the knife channel is now part of the cartridge and is replaced therewith. In turn the channel is open to one side in the sealing jaws and also in the hinge area cleaning openings can be provided.

Because at least in the preferred configuration the knife in the knife cartridge is unlocked during placement of the cartridge on the cartridge seat, the knife—the proximal blunt end of which can extend beyond the cartridge—can be simply inserted into the knife channel of the instrument by a shifting movement. Thereby an operating device can come in engagement with a respective coupling structure of the knife. For example, the coupling structure can be a recess in which a tappet of the operating device latches as soon as this recess is shifted in the range of the operating device.

In an embodiment of the invention the knife can also be completely positioned in the cartridge in a disassembled condition. In such an embodiment the handling is especially easy and safe.

Many modifications can be made to the instrument described so far. For example, the knife can be held in the knife cartridge in a manner biased toward its safe position, wherein the blade of the knife is in the inner space of the housing of the knife cartridge in the safe position. For biasing toward the safe position a spring element can be provided, e.g. in the form of a pressure spring, a tension spring, a magnet or the like.

It is also possible that the knife cartridge and the operating device are combined in a cartridge that can be removed from the instrument as a whole.

It is further possible to combine the knife cartridge with the operating device and a handle such that this extended knife cartridge forms a proximal part of the jaw.

It is also advantageous, if the tool parts of the sealing tool are immovably connected with the jaws. The knife cartridge is then the only part that can be simply removed from the instrument, which avoids confusion and operating errors. Particularly the knife cartridge and the tool parts are assemblies that are separated from each other and are not rigidly connected with each other.

Further possibilities of positioning the cartridge are available. For example, the cartridge seat and thus the cartridge can be arranged in the hinge area of the instrument. Due to this proximity of the cartridge to the clamping area of the instrument in which biological tissue is grasped, the movement path and/or the length of the knife are short. Thus, the cartridge can be miniaturized.

It is, however, common to all embodiments that respective locking means are provided for reliable locking of the knife cartridge at the instrument, e.g. in the form of latching means. These are preferably arranged in the area of the distal end of the cartridge seat in order to simplify handling of the cartridge during cartridge replacement. Preferably the movement direction during attachment of the knife cartridge at the jaw, as well as during disconnection of the knife cartridge from the jaw, is orientated transverse to the movement direction of the knife.

BRIEF DESCRIPTION OF THE DRAWINGS

Further details of embodiments of the invention are subject of the dependent claims, the drawings or the description.

The drawings show.

DETAILED DESCRIPTION

Figure 1:
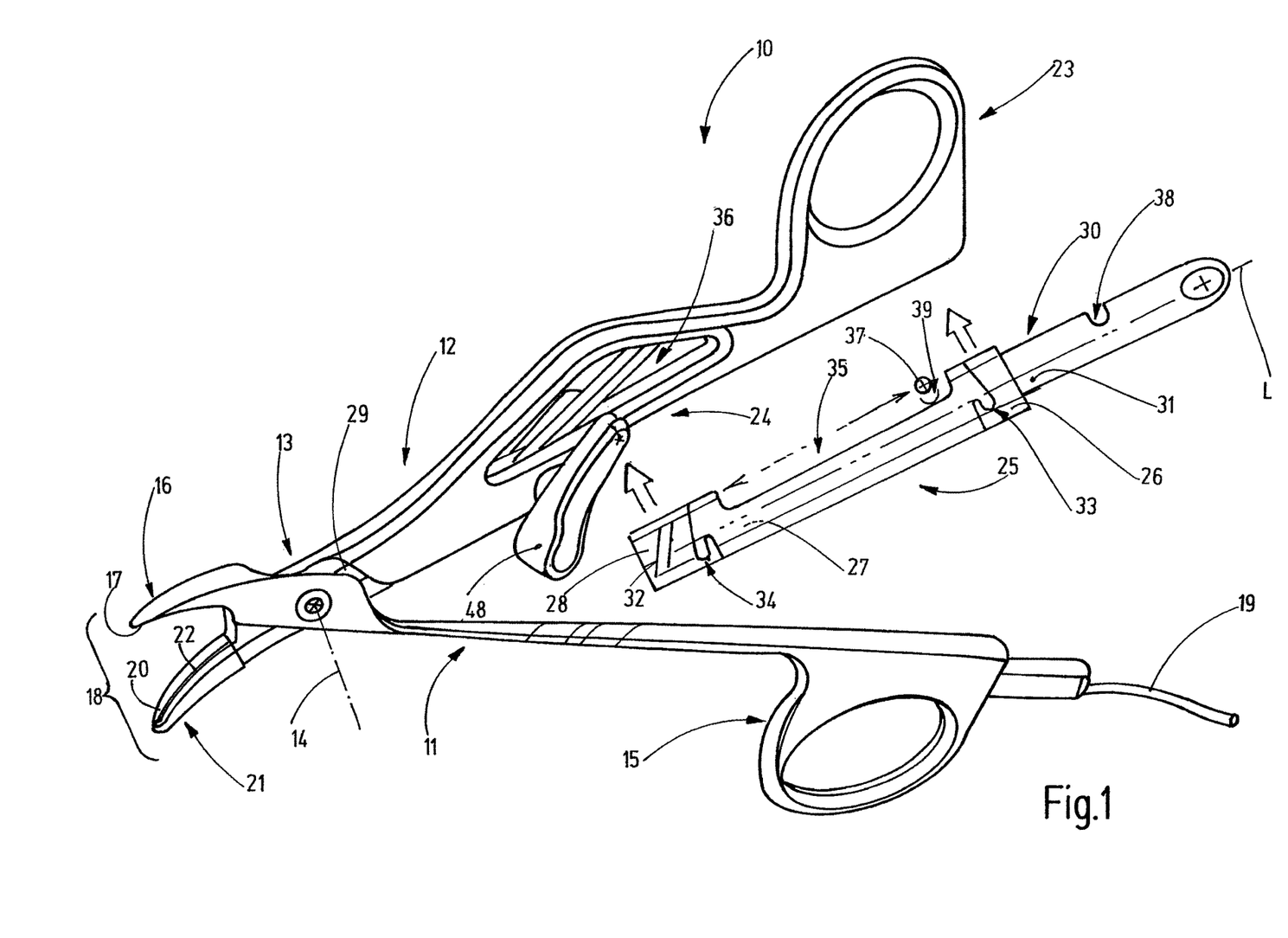
FIG. 1 the inventive sealing instrument with knife cartridge in a schematic perspective illustration, FIG. 2, 2a a knife cartridge and the assigned cartridge seat in a simplified basic illustration in perspective side view, FIG. 3, 3a a cartridge seat of a jaw and the knife cartridge in non-latched condition in a simplified cross-sectional illustration, FIG. 4, 4a the cartridge seat and the cartridge in latched condition in cross-sectional illustration according to FIG. 3, FIG. 5 a sealing instrument with assigned knife cartridge in a partly perspective explosion illustration, FIG. 6a-c the knife cartridge for the instrument according to FIG. 5 with reciprocal interlocking in different positions in a sectional illustration in each case, FIGS. 7 to 9 modified embodiments of the inventive sealing instrument.

In FIG. 1 a sealing instrument 10 is illustrated that comprises a first jaw 11 and a second jaw 12 that are pivotably supported relative to each other by means of a hinge 13. For example, hinge 13 can define a pivot axis 14 that is orientated transverse to the jaws 11, 12.

The first jaw 11 comprises a leg that carries a handle 15 at its proximal end. The distal end 16 of the jaw 11 that is thus positioned beyond the axis 14 with view from a user comprises a first tool part 17 that is part of a sealing tool 18. For this the first tool part 17 comprises at least one sealing electrode that can be supplied with a current via a cable 19 extending away from the proximal end of the first jaw to a non-illustrated apparatus.

A second tool part 20 that is formed by a sealing electrode attached to a distal end 21 of the second jaw 12 is also part of the sealing tool 18. Just like the first tool part 17, also the second tool part 20 comprises a slot 22 along which a knife can move in order to dissect a vessel or other tissue grasped between the tool parts 17, 20 and sealed by the effect of current. The second jaw 12 comprises a handle 23 at its proximal end, such that the instrument 10 can be handled in a way like a scissors or forceps.

In the section between the hinge 13 and the handle 23 of the second jaw 12 a cartridge seat 24 is configured that serves for reception of a knife cartridge 25.

The knife cartridge 25 comprises a housing 26 that encloses an inner space 27. The housing 26 can have a substantially longitudinally cuboid principle shape through which a knife channel 28 extends longitudinally. This knife channel 28 is preferably arranged such that it is aligned with a knife channel 29 provided at the second jaw 12.

A knife 30 is longitudinally shiftably arranged in the inner space 27, wherein a blunt section 31 can extend out of the housing 26. At the part of the knife 30 inside the housing 26 a blade 32 is configured that can extend, e.g. transverse to the longitudinal direction L of the knife 30. The longitudinal direction L is concurrently the movement direction of the knife 30.

The housing is preferably provided with attachment means, e.g. latching means 33, 34 to which respective counter structures are assigned configured at the cartridge seat 24 that are not further illustrated in FIG. 1. The latching means 33, 34 can be, for example, latching tappets, latching webs, latching springs or other resilient elements.

The housing 26 can also be provided with a cutout 35 in order to allow access to the knife 30 for an operating device 36. The driven member of the operating device can be, for example, a tappet that is individually illustrated symbolically in FIG. 1 and that may engage a recess 38 of the knife 30. The knife 30 can further comprise additional recesses, e.g. a recess 39, that serve to lock the knife 30 in a safe position. This safe position is illustrated in FIG. 1. In this position the blade 32 is located in the inner space 27 of the housing 26.

Figure 3:
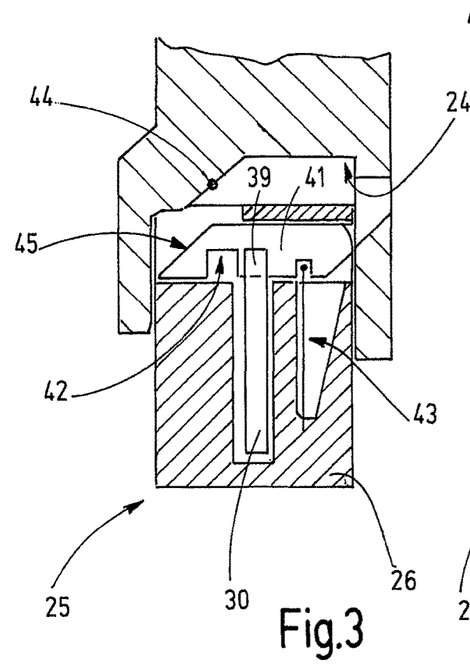

For locking the knife 30 in a safe position, a locking mechanism 40 can be provided that is configured to lock the knife 30 in the safe position as long as the knife cartridge 25 is not attached to the cartridge seat 24. Preferably the locking mechanism 40 is further configured such that it locks the knife cartridge 25 at the cartridge seat 24 at least as long as the knife 30 is not in its safe position. For this a movable blocking element 41 can be provided that is assigned to the knife cartridge 25. For example, the blocking element 41 can be a blocking latch or blocking pin that is shiftable transverse to the movement direction L of the knife 30 and that extends through the recess 39 of the knife 30 (FIGS. 1 and 3). Alternatively, the locking element can be configured integrally with the knife cartridge 25, e.g. as pivotably supported latch. The pivotable end of the latch can serve as blocking tappet.

Figure 4:
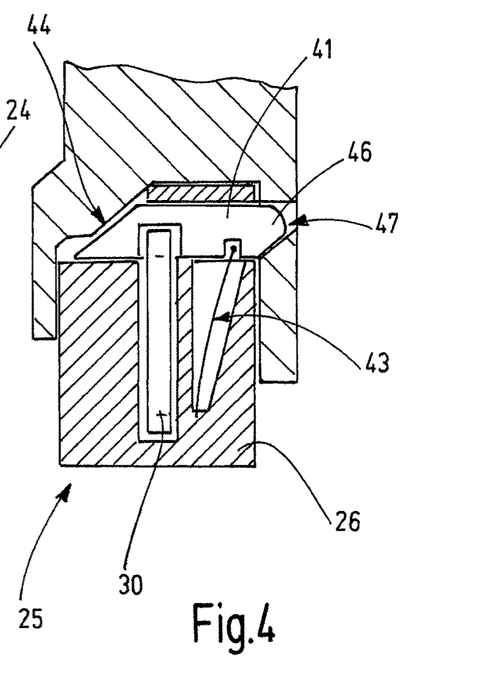

The blocking element 41 can comprise a recess 42 that can be brought in alignment with the knife 30 by a respective movement of the blocking element 41, as illustrated in FIG. 4. In this position the blocking element 41 releases a longitudinal movement of the knife 30. For reliable blocking of the knife 30 in a safe position, if the knife cartridge 25 is removed from the instrument 10, the blocking element 41 can be biased by a spring means 43 toward its blocking position shown in FIG. 3. In case of the integral configuration of the knife cartridge 25 and the blocking element 41, the latch itself can form the spring means.

At the cartridge seat 24 in addition an unlocking element 44 can be arranged, e.g. in form of an inclined surface or a projection, wherein an actuating surface 45 is provided at the blocking element 41 which is assigned to the unlocking element 44. For example, the actuating surface 45 can be arranged obliquely to the movement direction of the blocking element 41.

The blocking element 41 can further comprise a blocking tappet 46 that engages into a blocking opening 47 provided at the cartridge seat 24 and thus locks the knife cartridge 25 at the cartridge seat 24 as soon as the knife 30 is unlocked (i.e. when the recess 42 is aligned with the knife 30 as illustrated in FIG. 4).

Figure 2:
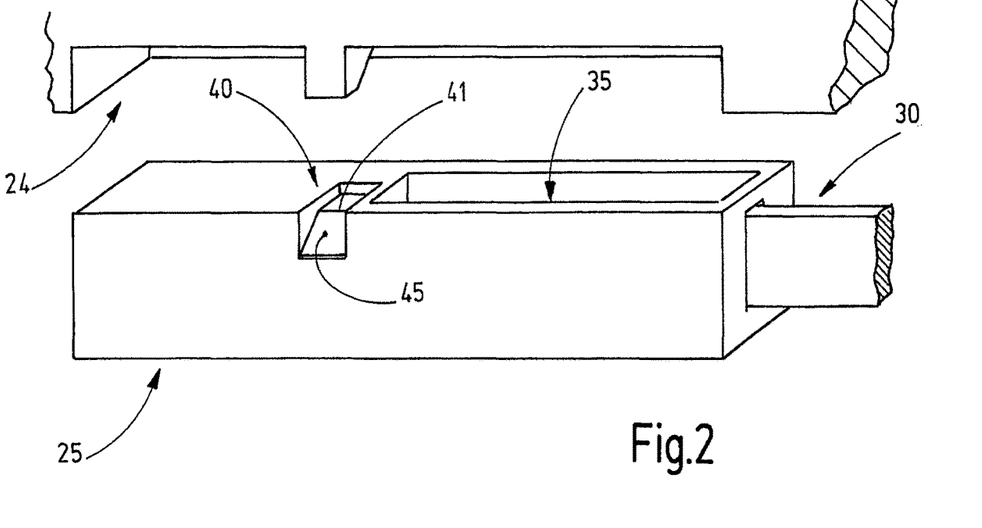
Figure 2A:
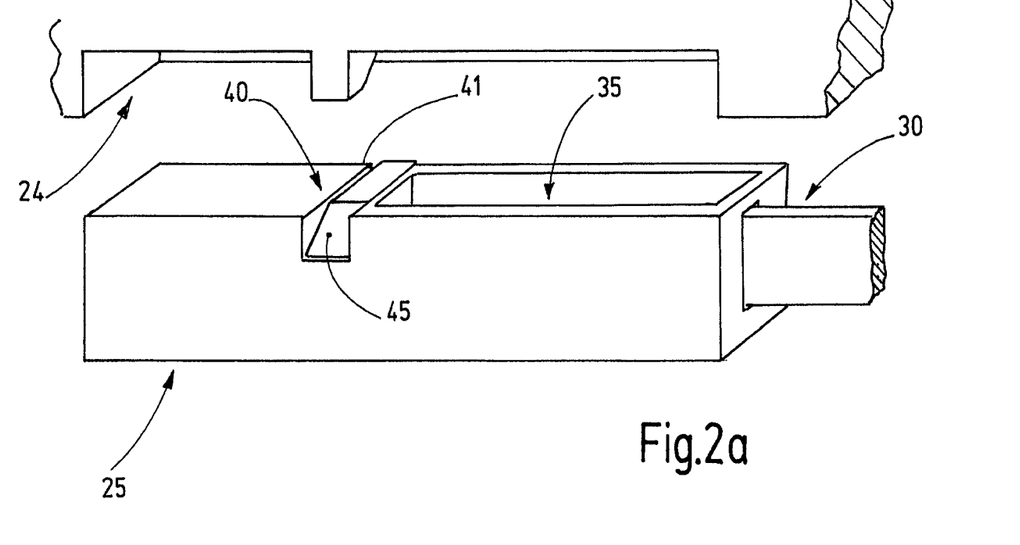
Figures 3A, 4A:
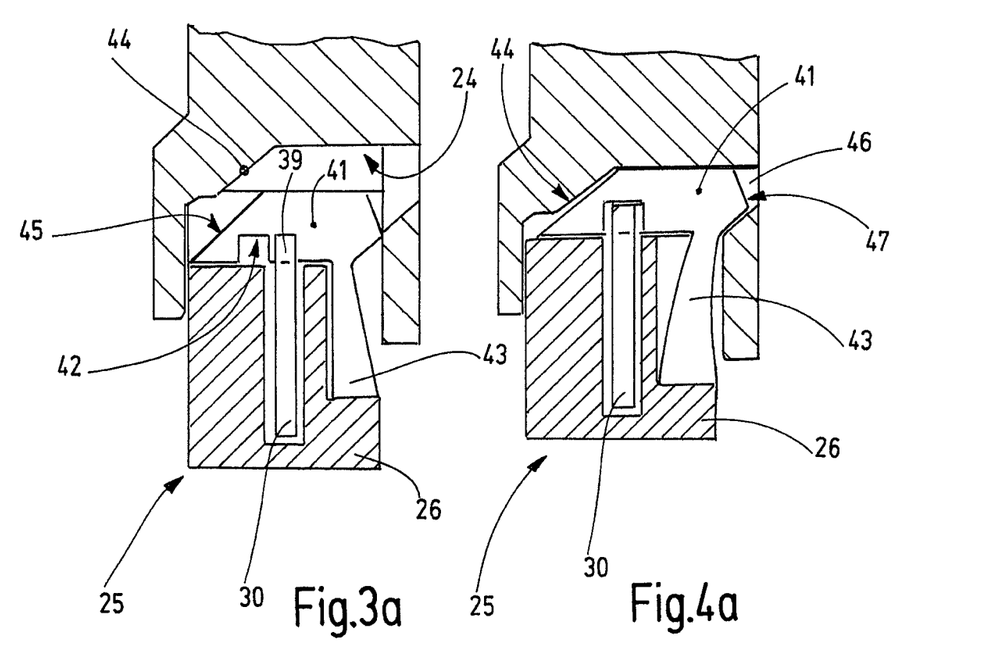

FIGS. 2a, 3a and 4a illustrate a sealing instrument 10 and a knife cartridge 25 in modified embodiment for which the description of the embodiment according to FIGS. 2 to 4 applies accordingly. However, the spring means 43 is integrally formed with the blocking element 41 and/or the housing 26 in this knife cartridge 25.

The instrument 10 and the assigned knife cartridge 25 described so far operate as follows:

For clarification it is assumed first that the instrument 10 and the assigned knife cartridge 25 are provided individually. The knife cartridge 25 comprises the knife 30 in safe position in which the knife 30 is preferably locked. Thus, the knife cartridge 25 is safe to handle. At most the blunt section 31 projects from the housing 26, whereas the blade 32 is held in the housing 26 in a safe manner.

For set-up of the instrument 10, the knife cartridge 25 is moved to the cartridge seat 24 and placed thereon. In doing so, the knife 30 is unlocked by a respective movement of the blocking element 41 that is transferred from the position illustrated in FIG. 3 in the position of FIG. 4. Thereby the knife cartridge 25 is concurrently locked at the cartridge seat 24. The longitudinal movement of the knife is, however, released now. Thereby the user of the knife 30 can grab the blunt part 31 and shift it through the knife channel 28 forward to the left in FIG. 1, such that the blade 32 enters the knife channel 29. Thereby the recess 38 can concurrently reach the area of the tappet 37, whereby the knife 30 couples to the operating device 36. The knife 30 blocks a return movement of the blocking element 41 in this position such that a reliable locking of the knife cartridge at the cartridge seat 24 is obtained as soon as the knife 30 is displaced such that its blade 32 exits the housing 26. The instrument 10 is now ready for operation. Tissue sections, particularly vessels, can be grasped by the sealing tool 18 and can be sealed by application of current between the two tool parts 17, 20. By operation of a hand lever 48 of the operating device 36, the knife is shifted through the slot 22 in order to cut the sealed vessel by means of the tappet 37 engaging in the recess 38.

Thereby the knife 30 can be somewhat flexible in order to follow the curvature of the slot 22, if the jaws have a curvature to the side.

For replacement of the knife cartridge 25 the actuating lever 48 is first brought in the unlocking position such that the tappet 37 moves out of the recess 38. The knife 30 can now be pulled back up to a stop. In the position reached thereby the recess 39 is aligned again with the blocking element 41 such that the knife 30 no longer blocks a movement of a blocking element 41 transverse to the knife 30. In this condition the knife cartridge 25 can be removed from the cartridge seat 24, wherein the blocking element 41 returns in its blocking position under the effect of the spring element 43. Concurrently the blocking tappet 46 moves out of the blocking opening 47, whereby the release of knife cartridge 25 is possible. Thereby the spring means 43 is optional. It serves predominantly for the support of the release movement and to retain the blocking element 41 permanently in blocking position.

It is clear that other locking mechanisms are possible. For example, the blocking element 41 can only be provided for blocking of the knife movement and locking of the knife cartridge 25 at the cartridge seat 24 can be omitted. Also the use of a pivotably moveable blocking element is possible that can be integrally configured with the housing 26, for example.

Figures 5, 6A, 6B, 6C:
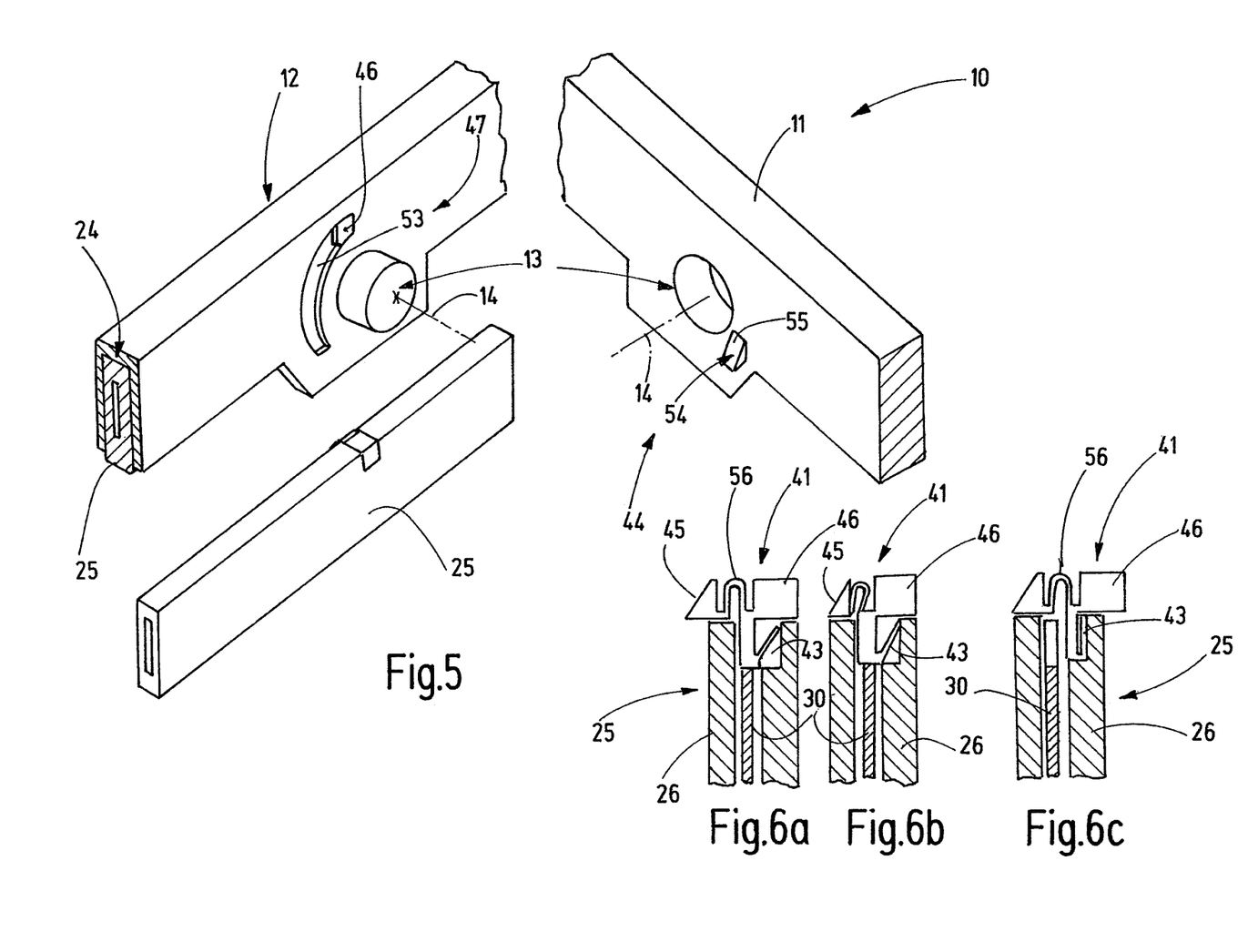

A further embodiment of the sealing instrument 10 is illustrated in explosion illustration in FIG. 5 including the knife cartridge 25 that is to be located therein, wherein the jaws 11, 12 are spread apart. The jaws 11, 12 are thereby illustrated cut on both sides of their hinge 13 for approving clarity. As apparent the second jaw 12 comprises the cartridge seat 24 in which the knife cartridge 25 can be placed. For example, the cartridge seat 24 can be formed by a groove open at a narrow side of the jaw 12 in which the knife cartridge 25 fits.

Concentrically to the hinge axis 14 an arc-shaped latch groove 53 is configured that serves as blocking opening 47 and extends through a limiting wall of the cartridge seat 24. FIG. 5 illustrates the blocking element 41 as it is latched with its blocking tappet 46 in the latch groove 53.

The jaw 11 comprises a cam 54 forming the unlocking element 44 and fitting in the latch groove 53. During pivoting the two jaws 11, 12 against each other it moves along the latch groove 53. The cam 54 comprises an actuating surface 55 that is inclined with regard to the hinge axis 14.

The blocking element 41 and its function is apparent from FIGS. 6a to 6c. As can be seen, it comprises a blocking tappet 46 that is biased in a blocking position in which the knife 30 is blocked, by means of a spring latch or another spring means 43 arranged or formed at the blocking element 41 or also at the housing 26.

An actuating surface 45 at an actuating piece connected with the blocking tappet 46 via a spring element 56 is in turn part of the blocking element 41. The spring element 56 can be integrally formed with the actuating element and/or the blocking tappet 46.

FIG. 6a illustrates a blocking element 41 in a rest position. The spring means 43 keeps the blocking element 41 in a blocking position in which the knife 30 is locked against longitudinal movements.

If the knife cartridge 25 is inserted in the cartridge seat 24, a flank of the cartridge seat 24 concurrently urges the actuating surface 45 in the position illustrated in FIG. 6b. However, the blocking tappet 46 extending along the wall opposite the cartridge seat 24 impedes a movement of the blocking element 41 in release position such that the knife 30 remains locked according to FIG. 6b.

As soon as the knife cartridge 25 has reached its desired position, the blocking tappet 46 reaches the latch groove 53 such that its latches into the latch groove 53 under the effect of the spring element 56 that now relaxes again. In this position the blocking element 41 locks the knife cartridge 25 at the cartridge seat 24.

The two jaws 11, 12 can be pivoted during the use of the instrument on the patient relative to each other without contact of the cam 54 against the blocking tappet 46. If the sealing instrument 10 is an open surgical instrument similar to the illustration of FIG. 1, thereby the latch groove 53 and thus the free travel path of the cam 54 in the latch groove 53 is at least as long that a user also with a largest considerable hand can move the handles 15, 23 away from each other about at least a span (distance between middle finger and thumb) without running of the cam 54 against the blocking tappet 46. If the two jaws 11, 12 are, however, pivoted further away from each other, the cam 54 acts with its actuating surface 55 on the blocking tappet 46 and urges it toward the inside. This is only achieved with the knife 30 being retracted, i.e. placed inside the housing 26. The blocking element 41 of the knife cartridge 25 is thus brought from the position according to FIG. 6c in the position according to FIG. 6b such that the knife 30 locks and the knife cartridge 25 in the cartridge seat 24 is released for removal. It can now be removed.

Figure 7:
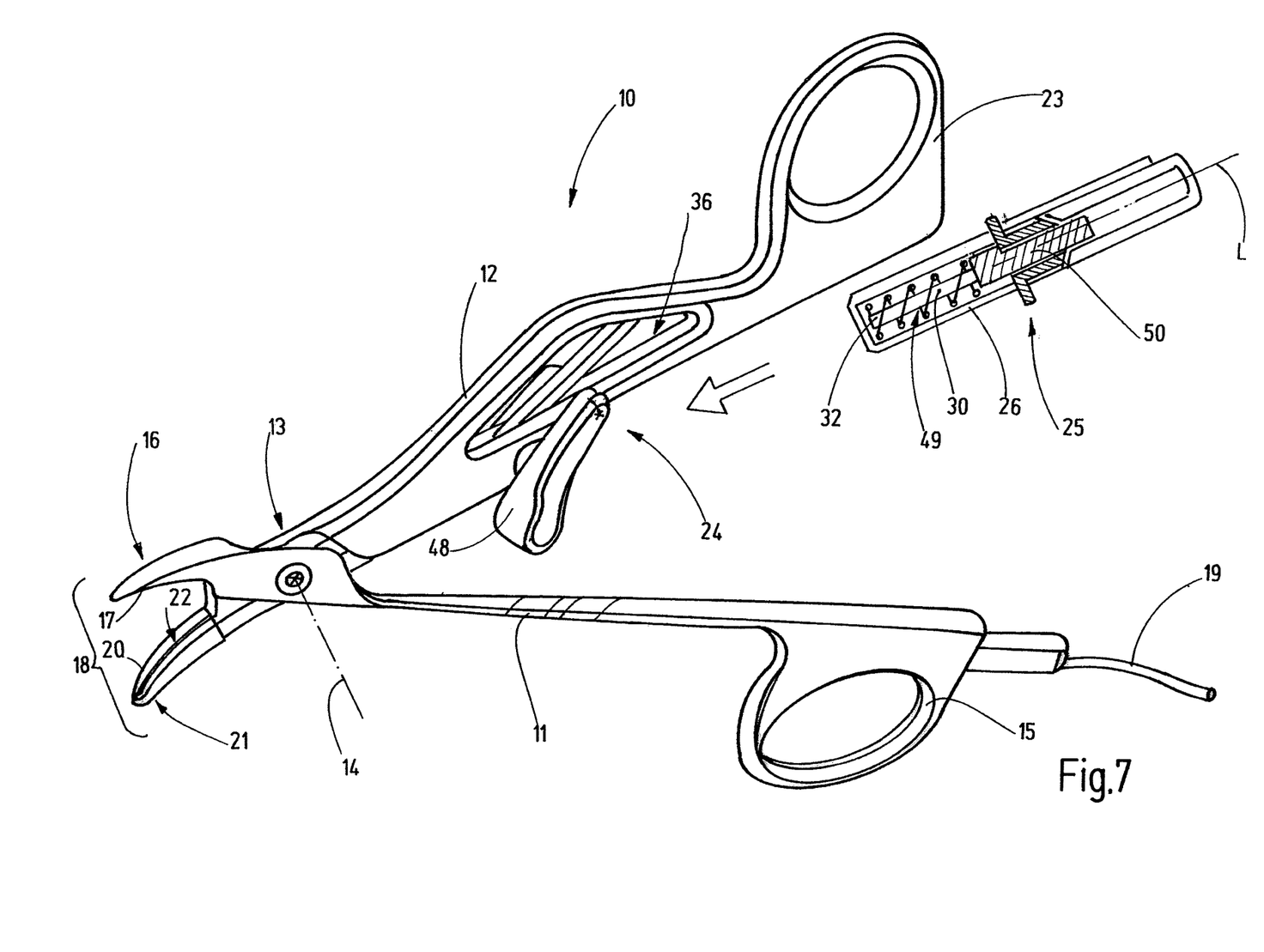

It is further possible to omit a locking mechanism and to retain the knife 30 in a safe position, e.g. by means of energy-storing elements such as a magnet or a spring element 49, as schematically illustrated in FIG. 7. The knife 30 can be held in a base 50 there that comprises extensions projecting out of the housing 26. These extensions can be used in order to move the knife 30 manually and temporarily out of the housing 26 for inspection purposes. In addition, the extensions can serve for the engagement of the operating device 36. Apart therefrom the description with regard to the embodiments according to FIG. 1 applies accordingly for the embodiment of instrument 10 according to FIG. 7 on the basis of the already introduced reference numerals.

Figure 8:
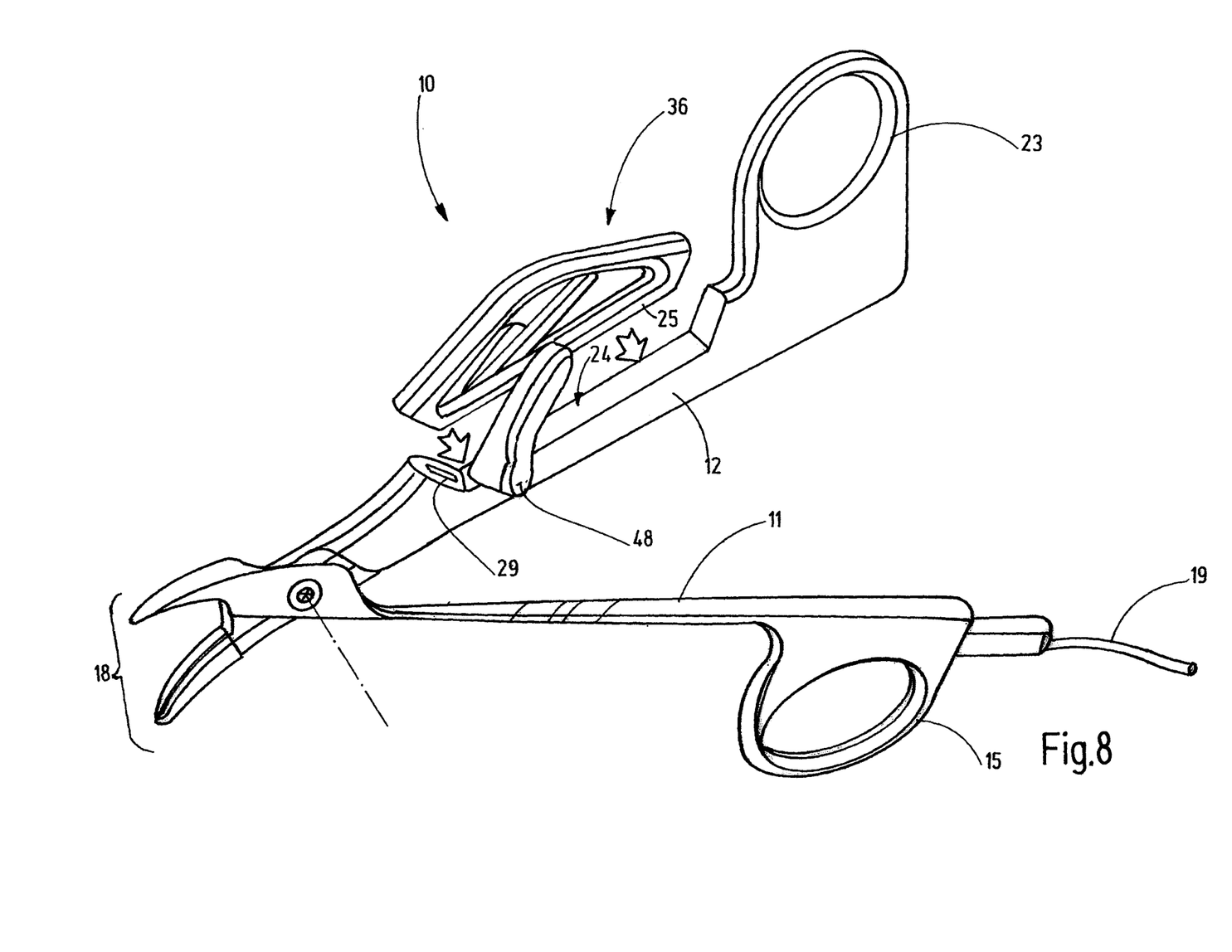

In a further modified embodiment of the instrument 10 the operating device 36 can also be combined with the knife cartridge 25 to one assembly, as illustrated in FIG. 8. The cartridge seat 24 receives the unit consisting of the operating device 36 and the knife cartridge, wherein suitable latch and positioning means are provided in order to bring the knife channel 28—that is not further illustrated in FIG. 8—in alignment with the knife channel 29.

Also in this embodiment a locking mechanism can be provided that allows the operation of the operating lever 48 and thus an extension of the knife only, if the knife cartridge 25 is correctly connected with the cartridge seat 24. Apart therefrom, also here the above description with regard to the other embodiments of the invention applies in addition.

Figure 9:
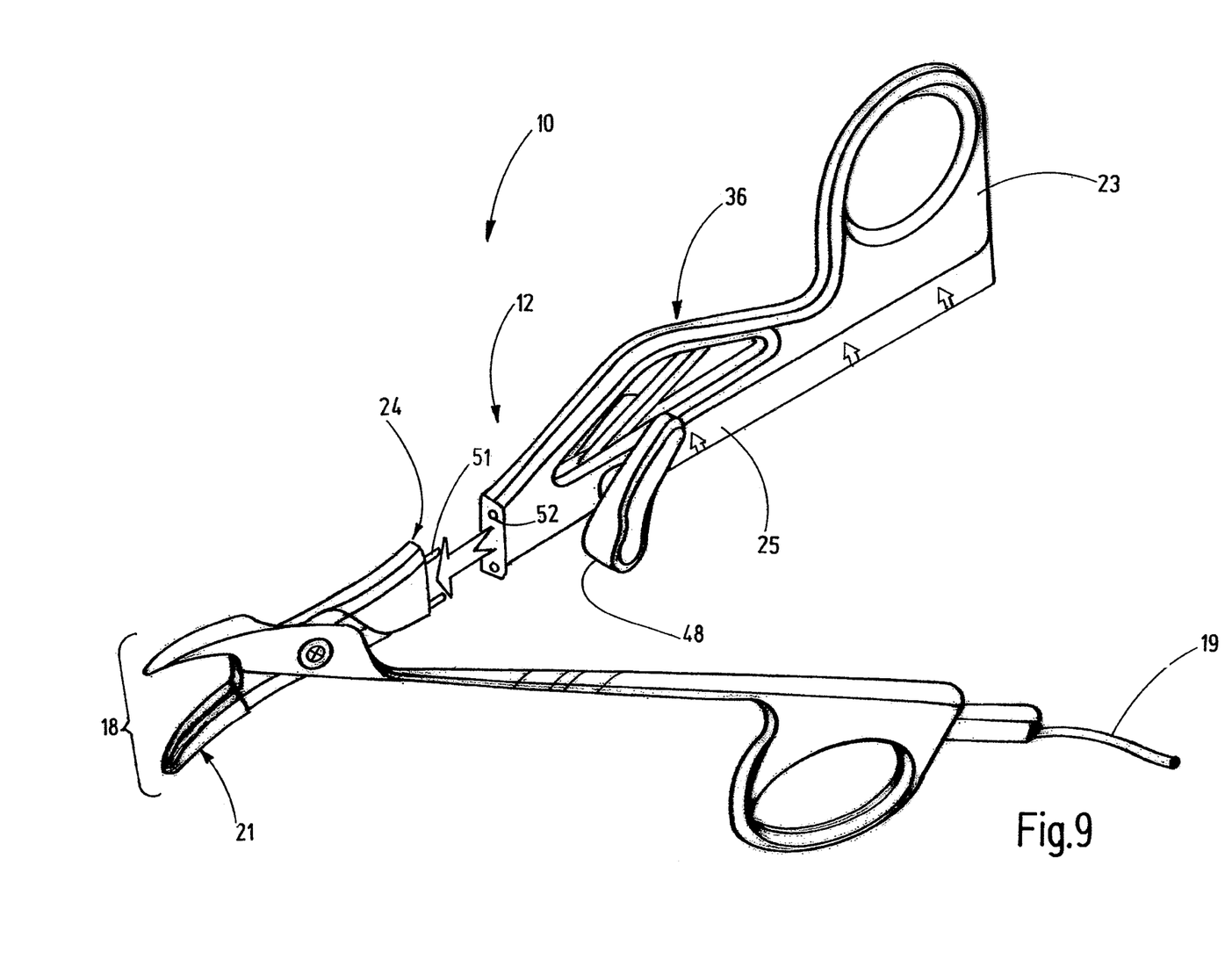

FIG. 9 illustrates a further modified embodiment of the instrument 10 in which the knife cartridge 25 does not only comprise the operating device 36, but in addition also the handle 23. The cartridge seat 24 is thus concurrently a connection location at which the force for closing the sealing tool 18 is transferred from the proximal part of the jaw 12 to the distal part 21 thereof. Thus, the knife cartridge 25 forms the proximal part of the jaw 12.

Also in this embodiment of the instrument 10 again a locking mechanism can be provided that only releases the operation of the knife that is an extension thereof out of the knife cartridge 25, if the knife cartridge 25 is correctly connected with the cartridge seat 24. For this one or more unlocking pins 50 can be provided, for example, that are provided at the cartridge seat 24 and engaged in respective openings 51 in order to unlock the movement of the knife and/or create a coupling between the operating device 36 and the knife.

The inventive concept provides an instrument 10 that comprises a cartridge seat 24 for a knife cartridge 25. The knife cartridge 25 holds a knife 30, preferably in protected safe position in which the blade 32 of the knife 30 is reliably retained inside the housing 26 of the knife cartridge 25 during non-use, particularly if the knife cartridge 25 is not inserted in the sealing instrument 10.

This concept leads to an increased handling safety for the medical staff.

LIST OF REFERENCE SIGNS 10 sealing instrument
11 first jaw
12 second jaw
13 hinge
14 pivot or hinge axis
15 handle of first jaw 11
16 distal end of first jaw 11
17 first tool part
18 sealing tool
19 cable
20 second tool part
21 distal end of second jaw 12
22 slot
23 handle of second jaw 12
24 cartridge seat
25 knife cartridge
26 housing of knife cartridge 25
27 inner space of housing 26
28 knife channel of housing 26
29 knife channel of second jaw 12
30 knife
31 blunt section of knife 30
32 blade of knife 30
33, 34 latching means
35 cutout
36 operating device
37 tappet
38, 39 recess in the edge of the knife 30
40 locking mechanism
41 blocking element
42 recess in the blocking element
43 spring means
44 unlocking element
45 actuating surface
46 blocking tappet
47 blocking opening
48 actuating lever
49 spring element
50 base
51 unlocking pin
52 opening
53 latch groove
54 cam
55 actuating surface
56 spring element
L longitudinal and shift direction of knife 30

The invention claimed is:

1. A sealing instrument (10), comprising:
   a first jaw (11) that comprises a first tool part (17) of a sealing tool (18) at its distal end (16);
   a second jaw (12) that is pivotably supported relative to the first jaw (11) and that comprises a second tool part (20) of the sealing tool (18) at its distal end (21);
   a cartridge seat (24) that is configured to receive a knife cartridge (25);
   a knife cartridge, the knife cartridge comprising:
   a housing (26) that encloses an inner space (27); and
   a knife (30) that comprises at least one cutting edge (32) and that comprises an operating device (36) or a coupling device (38) for connection to an operating device (36);
   wherein the knife (30) is movably arranged in the knife cartridge (25) for being shifted from a first position in which the at least one cutting edge (32) is arranged in the inner space (27) into a second position in which the at least one cutting edge (32) is outside of the knife cartridge (25);
   a locking mechanism (40) of the knife cartridge that is arranged to be effective between the housing (26) and the knife (30);
   wherein the locking mechanism (40) comprises a blocking element (41) movably supported at or in the housing (26);
   wherein a blocking structure (39) formed at the knife (30) is configured for engagement with the blocking element (41); and
   wherein the blocking element (41) is configured to cooperate with an unlocking structure (44) formed at the cartridge seat (24) or the operating device (36).

2. The sealing instrument according to claim 1, wherein the locking mechanism (40) comprises an actuating surface (45) for unlocking.

3. The sealing instrument according to claim 1, wherein the locking mechanism (40) is configured for locking the knife cartridge (25) at the cartridge seat (24).

4. The sealing instrument according to claim 1, wherein the locking mechanism (40) is configured for reciprocal interlocking, wherein the blocking element (41) thereof is configured to lock the knife (30) in the knife cartridge (25) in a first position and the knife cartridge (25) at the cartridge seat (24) in a second position.

5. The sealing instrument according to claim 1, wherein the knife cartridge (25) comprises a knife channel (28) that is arranged in alignment with a knife channel (29) formed in the sealing instrument (10) when the knife cartridge (25) is attached to the cartridge seat (24).

6. The sealing instrument according to claim 1, wherein the knife cartridge (25) comprises a knife retraction device.

7. The sealing instrument according to claim 6, wherein the knife retraction device is a spring element (49) that is configured to bias the knife (30) toward a position in which the at least one cutting edge (32) of the knife (30) is in the inner space (27) of housing (26).

8. The sealing instrument according to claim 1, wherein the knife cartridge (25) is configured to form a proximal section of the second jaw (12) and comprises a handle (23).

9. The sealing instrument according to claim 1, wherein the knife (30) comprises the coupling device (38) for connection with a tappet (37) of the operating device (36).

10. A sealing instrument (10), comprising:
   a first jaw (11) that comprises a first tool part (17) of a sealing tool (18) at its distal end (16);
   a second jaw (12) that is pivotably supported relative to the first jaw (11) and that comprises a second tool part (20) of the sealing tool (18) at its distal end (21);
   a cartridge seat (24) that is configured to receive a knife cartridge (25);
   a knife cartridge, the knife cartridge comprising:
      a housing (26) that encloses an inner space (27);
      a knife (30) that comprises at least one cutting edge (32) and that comprises an operating device (36) or a coupling device (38) for connection to an operating device (36);
   wherein the knife (30) is movably arranged in the knife cartridge (25) for being shifted from a first position in which the at least one cutting edge (32) is arranged in the inner space (27) into a second position in which the at least one cutting edge (32) is outside of the knife cartridge (25);
   wherein the knife cartridge (25) comprises a knife retraction device; and
   wherein the knife retraction device is a spring element (49) that is configured to bias the knife (30) toward a position in which the at least one cutting edge (32) of the knife (30) is in the inner space (27) of housing (26).

11. The sealing instrument according to claim 10, further comprising a locking mechanism (40) of the knife cartridge that is arranged to be effective between the housing (26) and the knife (30) wherein the locking mechanism (40) comprises a blocking element (41) movably supported at or in the housing (26), wherein a blocking structure (39) formed at the knife (30) is configured for engagement with the blocking element (41), wherein the blocking element (41) is configured to cooperate with an unlocking structure (44) formed at the cartridge seat (24) or the operating device (36).

12. The sealing instrument according to claim 11, wherein the locking mechanism (40) is configured for locking the knife cartridge (25) at the cartridge seat (24).

13. The sealing instrument according to claim 11, wherein the locking mechanism (40) is configured for reciprocal interlocking, wherein the blocking element (41) thereof is configured to lock the knife (30) in the knife cartridge (25) in a first position and the knife cartridge (25) at the cartridge seat (24) in a second position.

14. The sealing instrument according to claim 10, wherein the knife cartridge (25) comprises a knife channel (28) that is arranged in alignment with a knife channel (29) formed in the sealing instrument (10) when the knife cartridge (25) is attached to the cartridge seat (24).

15. The sealing instrument according to claim 10, wherein the knife cartridge (25) is configured to form a proximal section of the second jaw (12) and comprises a handle (23).

16. The sealing instrument according to claim 10, wherein the knife (30) comprises the coupling device (38) for connection with a tappet (37) of the operating device (36).

* * * * *